(12) United States Patent
Basko et al.

(10) Patent No.: US 10,835,568 B1
(45) Date of Patent: Nov. 17, 2020

(54) FEED AND METHOD FOR THE TREATMENT OF COPROPHAGIA

(71) Applicant: Garmon Corporation, Temecula, CA (US)

(72) Inventors: Ihor Basko, Kapaa, HI (US); Jodi Hoefler, Menifee, CA (US)

(*) Notice: Subject to any disclaimer, the term of this patent is extended or adjusted under 35 U.S.C. 154(b) by 0 days.

(21) Appl. No.: 16/202,070

(22) Filed: Nov. 27, 2018

Related U.S. Application Data

(63) Continuation of application No. 15/365,470, filed on Nov. 30, 2016, now abandoned.

(60) Provisional application No. 62/261,615, filed on Dec. 1, 2015.

(51) Int. Cl.

| | |
|---|---|
| *A61K 36/88* | (2006.01) |
| *A61K 31/702* | (2006.01) |
| *A61K 35/742* | (2015.01) |
| *A61K 38/46* | (2006.01) |
| *A61K 38/47* | (2006.01) |
| *A61K 38/48* | (2006.01) |
| *A23K 20/189* | (2016.01) |
| *A61K 36/23* | (2006.01) |
| *A23K 20/10* | (2016.01) |
| *A61K 33/44* | (2006.01) |
| *A23K 50/40* | (2016.01) |
| *A61K 36/07* | (2006.01) |
| *A61K 9/00* | (2006.01) |

(52) U.S. Cl.
CPC .............. *A61K 36/88* (2013.01); *A23K 20/10* (2016.05); *A23K 20/189* (2016.05); *A23K 50/40* (2016.05); *A61K 9/0056* (2013.01); *A61K 31/702* (2013.01); *A61K 33/44* (2013.01); *A61K 35/742* (2013.01); *A61K 36/07* (2013.01); *A61K 36/23* (2013.01); *A61K 38/465* (2013.01); *A61K 38/47* (2013.01); *A61K 38/48* (2013.01); *C12Y 302/01001* (2013.01); *C12Y 302/01004* (2013.01)

(58) Field of Classification Search
None
See application file for complete search history.

(56) References Cited

PUBLICATIONS

Soave et al., "Coprophagy in Animals: A Review", The Cornell Veterinarian, vol. 81, pp. 357-364 (Year: 1991).*
Kim et al., "Canine exocrine pancreatic insufficiency treated with porcine pancreatic extract", Journal of Veterinary Science, vol. 6, pp. 263-266 (Year: 2005).*
Westermarck et al., "Effects of diet on clinical signs of exocrine pancreatic insufficiency in dogs", Journal of the American Veterinary Medical Association, vol. 228, pp. 225-229 (Year: 2006).*

* cited by examiner

*Primary Examiner* — Michelle F. Paguio Frising
(74) *Attorney, Agent, or Firm* — The Law Office of Austin Bonderer, PC; Austin Bonderer

(57) ABSTRACT

A method of treating corprophagia in animals is provided. The method includes providing a product having one or more of parsley leaf powder, *yucca schidigera*, white mushroom extract, and a combination of probiotic, prebiotic and one or more enzymes to an animal to treat coprophagia.

18 Claims, No Drawings

FEED AND METHOD FOR THE TREATMENT OF COPROPHAGIA

FIELD

The subject matter herein generally relates to supplements given to animals to decrease the scent and attractiveness of feces and/or Coprophagia in animals.

DETAILED DESCRIPTION

It will be appreciated that numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The description is not to be considered as limiting the scope of the embodiments described herein.

Several definitions that apply throughout this disclosure will now be presented.

The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "about" includes a range of plur or minus five at the degree of the most precise measurement. For example, about 3.4 mg would 3.4 mg plus or minus 0.5 mg. The term "comprising" means "including, but not necessarily limited to"; it specifically indicates open-ended inclusion or membership in a so-described combination, group, series and the like.

The disclosure is illustrated by way of example. It should be noted that references to "an" or "one" embodiment in this disclosure are not necessarily to the same embodiment, and such references mean "at least one".

The present disclosure is described in relation to domesticated cats and dogs. However, it is understood that the supplement and/or methods described herein can also be given to other animals in which the ingredients are not harmful. It is also to be understood that while the present disclosure is described in terms of a supplement, it is understood that the method and ingredients can be used in the actual food produced as the main source of these animals' diets.

Dog owners often complain about their pet dog eating stools of other animals, and especially eating cat stool out of their litter box. This behavior is particularly unnerving given that many dogs have a tendency to lick the face of their owners.

It is also well known that many supplements that are given to cats cannot also be given to dogs and vice versa. However, it does not mean that these animals are free from attraction to these poisonous supplements. This is a cause of concern in many dual pet households, as cats and dogs will seek out the items they desire. Cross feeding often results in a poisoned pet. Owners also tend to have a sense of unfairness when giving something that is construed as a treat or food to one pet and not the other. However, cat products and dog products are often not interchangeable.

Coprophagia in dogs, i.e., consuming other animal's stool, is a natural survival behavior. It can be triggered by a poor diet and resultant nutritional deficiencies (protein, fat, minerals, and enzymes), a diet that is difficult to digest and absorb nutrients, infestation by parasites and worms, and/or an imbalance within the microbiome of the GI system. The dog is "craving" what is missing, not necessarily from their diet, but their digestion. This behavior can also become habitual although all of the nutrient factors have been addressed.

It has been found that supplementing the diet with a combination of ingredients will decrease the behavior in dogs as they no longer desire additional nutrition.

It has also been found that a second prong will aid in the Coprophagia of dogs when living with other animals in the home, e.g. other dogs and cats. Dogs are greatly attracted to smells. Cat diets are high in fat and protein. The cat stools will have significantly high levels of hydrogen sulfide, indoles, scatoles and ammonia by-products of digestion. These compounds tend to attract the dogs. Modifying the aroma of the stools can make the smell less interesting to dogs. This can be accomplished by decreasing the skatoles in the stool. The ammonia compounds present in feces and their aromatic gasses also contribute to the smell. By increasing the digestive efficiencies of the cohabiting animals, the attractiveness of the feces is reduced. For example, if the digestive efficiency of a cohabitating cat is increased, there will be less fat and protein in the cat's feces Also making the taste and smell of the feces unappetizing to dogs will help decrease the dog's coprophagia It is also well known that many supplements that are given to cats cannot also be given to dogs and vice versa. However, it does not mean that these animals are free from attraction to these poisonous supplements. This is a cause of concern in many dual pet households, as cats and dogs will seek out the items they desire. Often times resulting in a poisoned pet and/or a frantic pet owner. Companies are often called by veterinarians asking the contents and effects of their products because a pet is brought into their office after getting into the supplements, treats and food of another animal.

Decreasing the attractiveness of the feces can involve several factors. Dogs being natural scavengers are greatly attracted to certain odors especially decaying food or meat and animal feces.

The typical commercial food diet that is fed to cats is high in fat and protein and contains ingredients (fish meal, meat by-products, corn gluten, and soybean meal) that intensify the smell of their feces.

Therefore, cat feces will emit high levels of hydrogen sulfide, indoles, scatoles and ammonia gasses that are attractive to dogs.

Fecal odor results from a complex combination and concentrations of volatile odoriferous compounds which may include: ammonia, amines, sulfides, fatty acids, esters, alcohols, aldehydes, and ketones.

The high amounts of ammonia compounds present in cat feces combined with aromatic sulfides contribute to the odor which attracts the dog.

Odor can be decreased by improving digestive functions. Some embodiments neutralize ammonia and sulfur, and absorb toxins and gaseous fecal odors by feeding the animal with a combination of: parsley leaf, *Yucca schidigera*, activated charcoal, FOS (e.g. Fructooligosaccharides), and probiotic (e.g. *Bacillus coagluans*).

Decreasing the dog's cravings can involve several factors. One goal of supplementation is to improve the metabolism and function of the GI system, mollify nutritional deficiencies, and subsequently assuage the "bad habits" through behavioral modification training. As the dog's nutritional and digestive needs are satisfied the behavior to eat feces will diminish. This can be considered "step one" in the process. A second step can also be employed to make the cat feces uninteresting by mollifying the attractive odors and/or modifying the taste and mouth feel.

Dysbiosis (bacterial imbalance of the microbiome, inflammation, bloating), intestinal parasites, ingestion of drugs (anti-acids), and inappropriate diets may hinder the digestion, absorption, and assimilation of nutrients in both the cat and the dog. This may create more hunger through stimulation of hormones in the stomach (ghrelin and gastrin). If a nutritional deficiency is present in the dog, the dog might be attracted to eating feces in the cat litter box in order to "supplement" its diet.

A healthier microbiome reflects better digestion and assimilation of ingested foods. The breakdown of starches, sugars, fats and proteins will improve the absorption of nutrients, leaving less waste of nutrients in the feces. The commensal bacterial health (microbiome) of the intestinal tract can be enhanced with the addition of probiotics and/or prebiotic supplements. Some embodiments comprise prebiotics (e.g. FOS); *Yucca schidigera*, *Agaricus bisporus* (Mannanoligosaccharides) and the probiotic (e.g. *Bacillus coagulans*).

FOS and *Agaricus bisporus*, together reduce indoles and phenol complexes in the feces of dogs and cats when ingested reflecting better health of the colon and its population of bacteria. *Yucca schidigera* absorbs toxic ammonia levels in the intestines thus promoting the health of the commensal bacterial population. *Yucca schidigera* has shown to decrease pathogenic bacteria and certain protozoan parasites in the intestinal tract.

Some embodiments comprise one or more enzymes to improve the breakdown and absorption of minerals from starches, assist fat and protein digestion and aid in sugar metabolism. Enzymes can include alpha-amylase, lipase, cellulase, and/or protease.

Some embodiments of the supplement will improve digestion both in dogs and cats. Thus these embodiments improve their ability to absorb nutrients from the food, decrease hunger, and decrease the amount the nutrients lost in the feces.

In turn, the decrease in the nutrient content of the feces will help decrease the odor; thus decreasing the attractiveness of the feces to the dog.

Embodiments of a method for treating coprophagia is discussed below.

One embodiment of preventing and/or treating coprophagia comprises feeding a supplement to one or more animals, wherein the supplement comprises parsley (e.g. parsley leaf), *Yucca schidigera*, Activated Charcoal, Fructooligosaccharides (FOS), and a probiotic. In some embodiments the probiotic can consist of *Bacillus coagluans*. In some embodiments, the one or more animals comprises a dog. In some embodiments, the one or more animals comprises a cat. In some embodiments, the one or more animals comprises a cat and a dog. In some embodiments, the cat and the dog are cohabitating. Some embodiments further comprise one or more enzymes.

One embodiment of preventing and/or treating coprophagia comprises feeding a supplement to one or more animals; wherein the supplement comprises prebiotics, *Yucca schidigera*, and Mannanoligosaccharides (MOS) with the addition of the probiotic. In some embodiments, the prebiotics comprise FOS. In some embodiment, the MOS comes in the form of a mushroom ingredient, *Agaricus bisporus*. In some embodiments, the probiotic comprises *Bacillus coagulans*. In some embodiments, the supplement further comprises enzymes. The enzymes may comprise alpha-amylase, lipase, cellulase, and/or protease. In some embodiments, the enzymes are provided by an embodiment of PPE consisting of, in other embodiments comprising, Amylase (18,560 SKBU/g); Protease (176,800 PU/g); Cellulase (600 CMCU/g); Lipase (1,680 LU/g); *Bacillus coagulans* (800 Million cfu/g); FOS [Inulin-80%] (24%); and Calcium Sulfate. In some embodiments, the one or more animals comprises a dog. In some embodiments, the one or more animals comprises a cat. In some embodiments, the one or more animals comprises a cat and a dog. In some embodiments, the cat and the dog are cohabitating.

To aid in deodorization, one embodiment of preventing and/or treating coprophagia comprises feeding a supplement to one or more animals, wherein the supplement comprises parsley, activated charcoal, *yucca*. In some embodiments, the one or more animals comprises a dog. In some embodiments, the one or more animals comprises a cat. In some embodiments, the one or more animals comprises a cat and a dog. In some embodiments, the cat and the dog are cohabitating.

Example 1

A supplement comprising, by weight, about 37.9% Parsley Leaf Powder; about 50.6% *Yucca* Powder; and about 6.3% of Activated Charcoal.

Example 2

A supplement comprising 41.79329 mg of Parsley Leaf Powder; 55.72468 mg of *Yucca* Powder; and 6.96531 mg of Activated Charcoal. A dosage may require one or more supplements or fractions thereof. In some embodiments, four supplements are considered to constitute a dosage.

To aid in the decrease in the smell, one embodiment of preventing and/or treating coprophagia comprises feeding a supplement to one or more animals, wherein the supplement comprises MOS, activated charcoal, *yucca*, probiotic. In some embodiments, the MOS comes in the form of a mushroom ingredient. The mushroom may be *Agaricus bisporus*. In some embodiments, the probiotic comprises *Bacillus coagulans*. In some embodiments, the one or more animals comprises a cat. In some embodiments, the one or more animals comprises a cat and a dog. In some embodiments, the cat and the dog are cohabitating.

Example 3

A supplement comprising, by weight, about 50.6% *Yucca* Powder; about 1.2% White Mushroom Extract (*Agaricus bisporus*); about 6.3% of Activated Charcoal and a probiotic.

Example 4

A supplement comprising 55.72468 mg of *Yucca* Powder; 1.37918 mg of White Mushroom Extract (*Agaricus bisporus*); 6.96531 mg of Activated Charcoal; and a probiotic. A dosage may require one or more supplements or fractions thereof. In some embodiments, four supplements are considered to constitute a dosage.

To aid in digestion, one embodiment of preventing and/or treating coprophagia comprises feeding a supplement to one or more animals; wherein the supplement comprises an enzyme, probiotic, MOS, *yucca*, prebiotic. In some embodiments, the prebiotics comprise FOS. In some embodiments, the MOS comes in the form of a mushroom ingredient. The mushroom may be *Agaricus bisporus*. In some embodiments, the probiotic comprises *Bacillus coagulans*. In some of the embodiments, the enzyme can comprise alpha-amylase, lipase, cellulase, and/or protease. In some embodiments, the enzymes, prebiotic, and probiotic are provided by a Probiotic Prebiotic Enzyme blend (PPE or PPE blend). In some embodiments, the one or more animals comprises a cat. In some embodiments, the one or more animals comprises a cat and a dog. In some embodiments, the cat and the dog are cohabitating.

Example 5

A supplement comprising, by weight, about 50.6% *Yucca* Powder; about 1.2% White Mushroom Extract (*Agaricus bisporus*); probiotic, prebiotic and enzyme. In some embodiments, the combination of probiotic, prebiotic and enzyme is about 1.1%, by weight, of the supplement.

Example 6

A supplement comprising, by weight, about 50.6% *Yucca* Powder; about 1.2% White Mushroom Extract (*Agaricus bisporus*); and 3.7% of PPE.

Example 7

A supplement comprising 55.72468 mg of *Yucca* Powder; 1.37918 mg of White Mushroom Extract (*Agaricus bisporus*); probiotic, prebiotic and enzyme. A dosage may require one or more supplements, or fractions thereof. In some embodiments, four supplements are considered to constitute a dosage.

Example 8

A supplement comprising 55.72468 mg of *Yucca* Powder; 1.37918 mg of White Mushroom Extract (*Agaricus bisporus*); and 4.13754 mg of PPE. A dosage may require one or more supplements or fractions thereof. In some embodiments, four supplements are considered to constitute a dosage.

To aid in altering the taste of the feces, one embodiment of preventing and/or treating coprophagia comprises feeding a supplement to one or more animals, wherein the supplement comprises *yucca*, MOS, activated charcoal. In some embodiments, the MOS comes in the form of a mushroom ingredient. The mushroom may be *Agaricus bisporus*. In some embodiments, the probiotic comprises *Bacillus coagulans*. In some embodiments, the one or more animals comprises a cat. In some embodiments, the one or more animals comprises a cat and a dog. In some embodiments, the cat and the dog are cohabitating.

Example 9

A supplement comprising, by weight, about 50.6% *Yucca* Powder; about 1.2% White Mushroom Extract (*Agaricus bisporus*); and about 6.3% of Activated Charcoal.

Example 10

A supplement comprising 55.72468 mg of *Yucca* Powder; 1.37918 mg of White Mushroom Extract (*Agaricus bisporus*); and 6.96531 mg of Activated Charcoal. A dosage may require one or more supplements or fractions thereof. In some embodiments, four supplements are considered to constitute a dosage.

In order to help with digestion and deodorizing and altering the smell and taste of feces, one embodiment of preventing and/or treating coprophagia comprises feeding a supplement to one or more animals, wherein the supplement comprises parsley, activated charcoal, *yucca*, MOS, probiotic, prebiotic, and an enzyme. In some embodiments, the MOS comes in the form of a mushroom ingredient. The mushroom may be *Agaricus bisporus*. In some embodiments, the probiotic comprises *Bacillus coagulans*. In some embodiments the prebiotics comprise FOS. In some of the embodiments, the enzyme can comprise alpha-amylase, lipase, cellulase, and/or protease. In some embodiments, the enzyme PPE. In some embodiments, the one or more animals comprises a cat. In some embodiments, the one or more animals comprises a cat and a dog. In some embodiments, the cat and the dog are cohabitating.

Example 11

A supplement comprising, by weight, about 37.9% of Parsley Leaf Powder; about 50.6% *Yucca* Powder; about 1.2% of White Mushroom Extract (*Agaricus bisporus*); about 6.3% Activated Charcoal; and about 3.7% PPE.

Example 12

A supplement comprising, by weight, about 37.9% of Parsley Leaf Powder; about 50.6% *Yucca* Powder; about 1.2% of White Mushroom Extract (*Agaricus bisporus*); about 6.3% Activated Charcoal; and probiotic, prebiotic and enzyme. In some embodiments, the combination of probiotic, prebiotic and enzyme is about 1.1%, by weight, of the supplement.

Example 13

A supplement comprising 41.79329 mg of Parsley Leaf Powder; 55.72468 mg of *Yucca* Powder; 1.37918 mg of White Mushroom Extract (*Agaricus bisporus*); and 6.96531 mg of Activated Charcoal; and 4.13754 mg of PPE. A dosage may require one or more supplements or fractions thereof. In some embodiments, four supplements are considered to constitute a dosage.

Example 14

A supplement comprising about 41.79329 mg of Parsley Leaf Powder; about 55.72468 mg of *Yucca* Powder; about 1.37918 mg of White Mushroom Extract (*Agaricus bisporus*); and about 6.96531 mg of Activated Charcoal; probiotic; prebiotic and enzyme. In some embodiments, the combination of probiotic, prebiotic and enzyme is about 1.241262 mg. A dosage may require one or more supplements or fractions thereof. In some embodiments, four supplements are considered to constitute a dosage.

Ingredients

It is understood that the types and/or amounts of the ingredients disclosed below are disclosed as being included in some embodiments of, and in addition to, the formulations defined above and below. For example, if an embodiment of a formulation is disclosed as comprising parsley, there are other embodiments, in addition to the ones disclosed above and below, that comprise the ingredients and/or amounts of parsley described below. A dosage is understood to include a daily suggested dosage and/or each dosage that is intended to be given two or more times a day. It is also understood that the dosage can be mixed in with feed during manufacture (e.g. Feed is premixed with the dosage such that it is integral with the feed), given alone as part of one or more items fed to an animal (e.g. a dosage can be contained in a single item or spread across several).

Parsley

In embodiments comprising parsley, amounts in a dosage can range from about 25 mg to about 1000 mg. In some embodiments, the dosage ranges from 100 mg to 500 mg.

*Yucca schidigera*

In embodiments comprising *Yucca schidigera*, amounts in a dosage can range from about 50 mg to about 2000 mg. In some embodiments, the dosage ranges from 75 mg to about 1000 mg.

Enzyme

In some embodiments comprising an enzyme, the enzyme comprises amylase, and amounts in a dosage can range from about 0.25 mg to about 50 mg, wherein the amylase has an effective activity in a range of about 13000 SKBU/g to about 24000 SKBU/g. In some embodiments, amounts in a dosage can range from about 1 mg to about 25 mg; wherein the amylase has an effective activity in a range of about 13000 SKBU/g to about 24000 SKBU/g.

In some embodiments comprising an enzyme, the enzyme comprises protease, and amounts in a dosage can range from about 0.25 mg to about 50 mg, wherein the protease has an effective activity in a range of about 132000 PU/g to about 220000 PU/g. In some embodiments, amounts in a dosage can range from about 1 mg to about 25 mg; wherein the protease has an effective activity in a range of about 132000 PU/g to about 220000 PU/g.

In some embodiments comprising an enzyme, the enzyme comprises Cellulase, and amounts in a dosage can range from about 0.25 mg to about 50 mg, wherein the cellulase has an effective activity in a range of about 450 CMCU/g to about 800 CMCU/g. In some embodiments, amounts in a dosage can range from about 1 mg to about 25 mg; wherein the cellulase has an effective activity in a range of about 450 CMCU/g to about 800 CMCU/g.

In some embodiments comprising an enzyme, the enzyme comprises lipase, and amounts in a dosage can range from about 0.25 mg to about 50 mg, wherein the lipase has an effective activity in a range of about 1200 LU/g to about 2100 LU/g. In some embodiments, amounts in a dosage can range from about 1 mg to about 25 mg; wherein the cellulase has an effective activity in a range of about 1200 LU/g to about 2100 LU/g.

In some embodiments comprising an enzyme, the enzyme comprises amylase, lipase, cellulase, and/or protease, and the amount of total enzymes in a dosage can range from about 1 mg to about 50 mg. Wherein amylase has an effective activity in a range of about 13000 SKBU/g to about 24000 SKBU/g; the protease has an effective activity in a range of about 132000 PU/g to about 220000 PU/g; the cellulase has an effective activity in a range of about 450 CMCU/g to about 800 CMCU/g; and the lipase has an effective activity in a range of about 1200 LU/g to about 2100 LU/g. In some embodiments, the enzyme comprises amylase, lipase, cellulase, and/or protease, and the amount of total enzymes in a dosage can range from about 5 mg to about 25 mg. Wherein amylase has an effective activity in a range of about 13000 SKBU/g to about 24000 SKBU/g; the protease has an effective activity in a range of about 132000 PU/g to about 220000 PU/g; the cellulase has an effective activity in a range of about 450 CMCU/g to about 800 CMCU/g; and the lipase has an effective activity in a range of about 1200 LU/g to about 2100 LU/g.

Probiotic

In some embodiments comprising probiotic, the probiotic comprises, or consists of, *Bacillus coagulans*. The amount of probiotic in a dosage is in a range from about 10,000 CFU to about 1.25 billion CFU. In some embodiments, the amount of probiotic in a dosage is in a range from about 1 million CFU to about 15 million CFU. In some embodiments, the amount of probiotic in a dosage is in a range from about 600 million CFU to about 1 billion CFU.

Prebiotic

In some embodiments comprising prebiotic, the prebiotic can be in a range greater than 0% to about 50% by weight. In other embodiments, the prebiotic can be in a range of about 5% to about 25% by weight. In some embodiments, the prebiotic comprises FOS. In some embodiments, the FOS is about 80% inulin.

MOS

In some embodiments comprising MOS, the MOS comes in the form of a mushroom ingredient. The amount of mushroom in a dosage is in a range from about 10 mg to about 1000 mg. In some embodiments, the amount of mushroom in a dosage is in a range from about 25 mg to about 500 mg. In some embodiments, the mushroom is *Agaricus bisporus*.

Activated Charcoal

In some embodiments comprising activated charcoal, the dosage is in a range in a range of about 5 mg to about 1000 mg. In some embodiments, the dosage is in a range of about 10 mg to about 500 mg.

PPE Blend (Also Referred to as PPE)

In some embodiments comprising a PPE blend, the PPE comprises from about 20% to about 40%, by weight, a mixture of probiotics, enzymes, and prebiotics. In some embodiments, the PPE comprises from about 25% to about 35%, by weight, a mixture of probiotics, enzymes, and prebiotics. In some embodiments, the PPE comprises from about 30%, by weight, a mixture of probiotics, enzymes, and prebiotics. In some embodiments the prebiotic is FOS. In some embodiments, the FOS is FOS (80% inulin). In some embodiments, FOS is about 24% of the mixture of probiotics, enzymes, and prebiotics. In some embodiments, the PPE comprises from about 80% to about 60%, by weight, CaSO4. In some embodiments, the PPE comprises from about 75% to about 65%, by weight, CaSO4. In some embodiments, the PPE comprises about 70%, by weight, CaSO4. In some embodiments, the PPE compromises about 2% to about 10%, by weight, a mixture of enzyme and probiotic. In some embodiments, the PPE compromises about 4% to about 8%, by weight, a mixture of enzyme and probiotic. In some embodiments, the PPE compromises about 6%, by weight, a mixture of enzyme and probiotic. In some embodiments, the enzyme comprises alpha-amylase, lipase, cellulase, and/or protease. In some embodiments, the probiotic comprises *Bacillus coagluans*.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of amount, size and arrangement of the parts within the principles of the present disclosure up to, and including, the full extent established by the broad general meaning of the terms used in the claims.

What is claimed is:

1. A method comprising:
providing a supplement comprising: parsley, *Yucca schidigera*, fructooligosaccharides (FOS) and/or mannanoligosaccharides (MOS), and a probiotic;
identifying a first animal as suffering from coprophagia disorder; and
feeding the supplement to the first animal to treat the coprophagia disorder.

2. The method of claim 1, wherein the supplement further comprises one or more enzymes.

3. The method of claim 1, wherein the first animal is a dog.

4. The method of claim 1, wherein the first animal is a cat.

5. The method of claim 1, further comprising feeding the supplement to a second animal, wherein the first animal is a dog and the second animal is a cat or a second dog.

6. The method of claim 5, wherein the second animal does not suffer from the coprophagia disorder.

7. The method of claim 1, wherein the supplement is premixed with dog food.

8. The method of claim 7, wherein the feeding the supplement to the first animal comprises supplying the first animal with the dog food.

9. The method of claim 1, wherein the supplement is premixed with cat food.

10. The method of claim 1, further comprising feeding the supplement to a second animal, wherein the feeding the supplement to the second animal comprises supplying the second animal with cat food.

11. A method of claim 1, wherein the supplement defines a weight; the parsley comprises parsley leaf powder, and the parsley leaf powder comprises about 37.9% of the weight; the *Yucca schidigera* comprises *yucca* powder, and the *yucca* powder comprises about 50.6% of the weight; and the MOS comprises white mushroom extract, and the white mushroom extract comprises about 1.2% of the weight.

12. A method of claim 11, further comprising feeding the supplement to a second animal.

13. A method of claim 11, further comprising feeding the supplement to a second animal, wherein the first animal is a dog and the second animal is a second dog or a cat.

14. A method of claim 1, wherein the parsley comprises parsley leaf powder, and the parsley leaf powder weighs about 41.7 mg; the *Yucca schidigera* comprise *yucca* powder, and the *yucca* powder weighs about 55.7 mg; and the MOS comprises white mushroom extract, and the white mushroom extract weighs about 1.3 mg.

15. A method of claim 14, further comprising feeding the supplement to a second animal.

16. A method of claim 14, further comprising feeding the supplement to a second animal, wherein the first animal is a dog and the second animal is a second dog or a cat.

17. A method of claim 1, further comprising feeding the supplement to a second animal.

18. A method of claim 1, further comprising feeding the supplement to a second animal, wherein the first animal is a dog and the second animal is a second dog or a cat.

* * * * *